United States Patent
Chu et al.

(10) Patent No.: US 10,989,660 B2
(45) Date of Patent: Apr. 27, 2021

(54) AUTOMATIC FLUORESCENCE DETECTION SYSTEM

(71) Applicant: CHROMA ATE INC., Taoyuan (TW)

(72) Inventors: Chien-Hsun Chu, Tao-Yuan Hsien (TW); Lan-Sheng Yang, Tao-Yuan Hsien (TW)

(73) Assignee: CHROMA ATE INC., Taoyuan (TW)

( * ) Notice: Subject to any disclaimer, the term of this patent is extended or adjusted under 35 U.S.C. 154(b) by 87 days.

(21) Appl. No.: 16/260,743

(22) Filed: Jan. 29, 2019

(65) Prior Publication Data
US 2019/0257753 A1   Aug. 22, 2019

(30) Foreign Application Priority Data
Feb. 22, 2018  (TW) .................................. 107105876

(51) Int. Cl.
*G01N 21/64* (2006.01)
*C12Q 1/6816* (2018.01)
*C12Q 1/686* (2018.01)

(52) U.S. Cl.
CPC ......... *G01N 21/6428* (2013.01); *C12Q 1/686* (2013.01); *C12Q 1/6816* (2013.01); *G01N 21/6452* (2013.01); *G01N 2021/6439* (2013.01)

(58) Field of Classification Search
None
See application file for complete search history.

(56) References Cited

U.S. PATENT DOCUMENTS

| | | | | |
|---|---|---|---|---|
| 2009/0009767 | A1* | 1/2009 | Boege | B01L 7/52 356/417 |
| 2009/0292479 | A1* | 11/2009 | Chuang | G01N 21/6452 702/19 |
| 2015/0323462 | A1* | 11/2015 | Ghosh | G01N 21/6486 435/29 |
| 2016/0241757 | A1* | 8/2016 | Cheng | A61B 5/7203 |
| 2019/0242569 | A1* | 8/2019 | Jiang | F21K 9/66 |

* cited by examiner

*Primary Examiner* — Hoon K Song
(74) *Attorney, Agent, or Firm* — Muncy, Geissler, Olds & Lowe, P.C.

(57) ABSTRACT

An automatic fluorescence detection system includes a base and an optical assembly. The base has a detecting region. The optical assembly includes a fluorescent image-capturing device, an illumination device and a field lens. The illumination device includes a first annular illumination module and a second annular illumination module surrounding a center axis of the fluorescent image-capturing device. Lights emitted by the first annular illumination module and the second annular illumination module travel along a light-traveling path to project onto the detecting region. A distance between the first annular illumination module and the center axis is smaller than that between the second annular illumination module and the center axis. The field lens is disposed in correspondence with the detecting region. Spacing between the field lens and the detecting region is ranged from 15.0 cm to 30.0 cm.

8 Claims, 8 Drawing Sheets

AUTOMATIC FLUORESCENCE DETECTION SYSTEM

This application claims the benefit of Taiwan Patent Application Serial No. 107105876, filed on Feb. 22, 2018, the subject matter of which is incorporated herein by reference.

BACKGROUND OF THE INVENTION

1. Field of the Invention

The invention relates to a fluorescence detection system, and more particularly to an automatic fluorescence detection system.

2. Description of the Prior Art

Quantitative real-time polymerase chain reaction (qPCR) is a method for detecting the total amount of products after each polymerase chain reaction (PCR) by measuring fluorescent dyes attaching on DNA during a DNA amplification process. Currently, the conventional fluorescence detection system usually applies an image-detecting method. This image-detecting method generally introduces an excitation light to radiate the DNA so as to make dyes fluorescent, then to filter the excitation light by a color-filtering plate, to capture the fluorescent image by an image sensor, and finally to realize the total amount of products in a test tube by analyzing corresponding light intensities.

However, in the conventional fluorescence detection system, the fluorescent image captured by the image sensor usually exhibits weaker fluorescence intensity at the rims of the image. Thus, a shortcoming of uniformity arises to the fluorescent image that presents different fluorescence intensities at a central portion and peripheral portions thereof, from which ill judgment upon DNA condensation would be foreseen. Recently, though an improved fluorescence detection system is developed to resolve the problems caused by the aforesaid uneven distribution of the fluorescence intensities, yet this improvement can be applied only to the situation that the fluorescence intensity of the rim reaches at least 80% fluorescence intensity of the central portion. In addition, since a severe limitation upon distances for related optical operations is required for this improved fluorescence detection system, thus it is hard to be upgraded to fulfill a possible automatic detection.

SUMMARY OF THE INVENTION

Accordingly, it is an object of the present invention to provide an automatic fluorescence detection system that can be automatically applied even to a fluorescent image having a weaker fluorescence intensity at a circumferential area.

In the present invention, the automatic fluorescence detection system includes a base and an optical assembly. The base has a detecting region. The optical assembly includes a fluorescent image-capturing device, an illumination device and a field lens. The illumination device includes a first annular illumination module and a second annular illumination module surrounding a center axis of the fluorescent image-capturing device. Lights emitted by the first annular illumination module and the second annular illumination module travel along a light-traveling path to project onto the detecting region. A distance between the first annular illumination module and the center axis is smaller than that between the second annular illumination module and the center axis. The field lens is disposed in correspondence with the detecting region. Spacing between the field lens and the detecting region is ranged from 15.0 cm to 30.0 cm.

In another aspect of the present invention, the automatic fluorescence detection system includes a base and an optical assembly. The base has a detecting region. The optical assembly includes a fluorescent image-capturing device, an illumination device and a concave reflector. The illumination device includes a first annular illumination module and a second annular illumination module surrounding a center axis of the fluorescent image-capturing device. A distance between the first annular illumination module and the center axis is smaller than that between the second annular illumination module and the center axis. The concave reflector is disposed in correspondence with the detecting region. Lights emitted by the first annular illumination module and the second annular illumination module are reflected by the concave reflector and then project onto the detecting region. Minimal spacing between the concave reflector and the detecting region is ranged from 15.0 cm to 30.0 cm.

In a further aspect of the present invention, the automatic fluorescence detection system includes a base, an optical assembly and a specimen-picking device. The base has a detecting region. The optical assembly includes a fluorescent image-capturing device, an illumination device and a field lens. Lights emitted by the illumination device travel along a light-traveling path to project onto the detecting region. The field lens is disposed in correspondence with the detecting region. The optical assembly has a work space between the field lens and the detecting region. The specimen-picking device is movably in the work space with respect to the base.

As stated, the automatic fluorescence detection system provided by the present invention adopts the illumination device having the annular illumination module to pair the field lens or the concave reflector, so that the optical field can be adjusted to make the excitation lights uniformly distributed. Thereupon, fluorescences with uniform intensities can be excited by the excitation lights upon DNA fragments at both the central portion and peripheral areas of the detecting region. Thus, the fluorescence intensity of the fluorescent image captured by the fluorescent image-capturing device at the peripheral area of the detecting region is about 90% the fluorescence intensity of the fluorescent image captured by the fluorescent image-capturing device at the central portion thereof, such that the testing of DNA density can be much accurate.

In addition, a sufficient work space between the field lens and the detecting region or between the concave reflector and the detecting region can be provided to accommodate the specimen-picking device. Thus, the automatic fluorescence detection system of this present invention applies the specimen-picking device to upload or download the centrifuge tubes containing DNA fragments, such that the automation in performing the quantitative real-time polymerase chain reaction cam be fulfilled.

All these objects are achieved by the automatic fluorescence detection system described below.

BRIEF DESCRIPTION OF THE DRAWINGS

The present invention will now be specified with reference to its preferred embodiment illustrated in the drawings, in which.

DESCRIPTION OF THE PREFERRED EMBODIMENT

The invention disclosed herein is directed to an automatic fluorescence detection system. In the following description, numerous details are set forth in order to provide a thorough understanding of the present invention. It will be appreciated by one skilled in the art that variations of these specific details are possible while still achieving the results of the present invention. In other instance, well-known components are not described in detail in order not to unnecessarily obscure the present invention.

Figure 1:
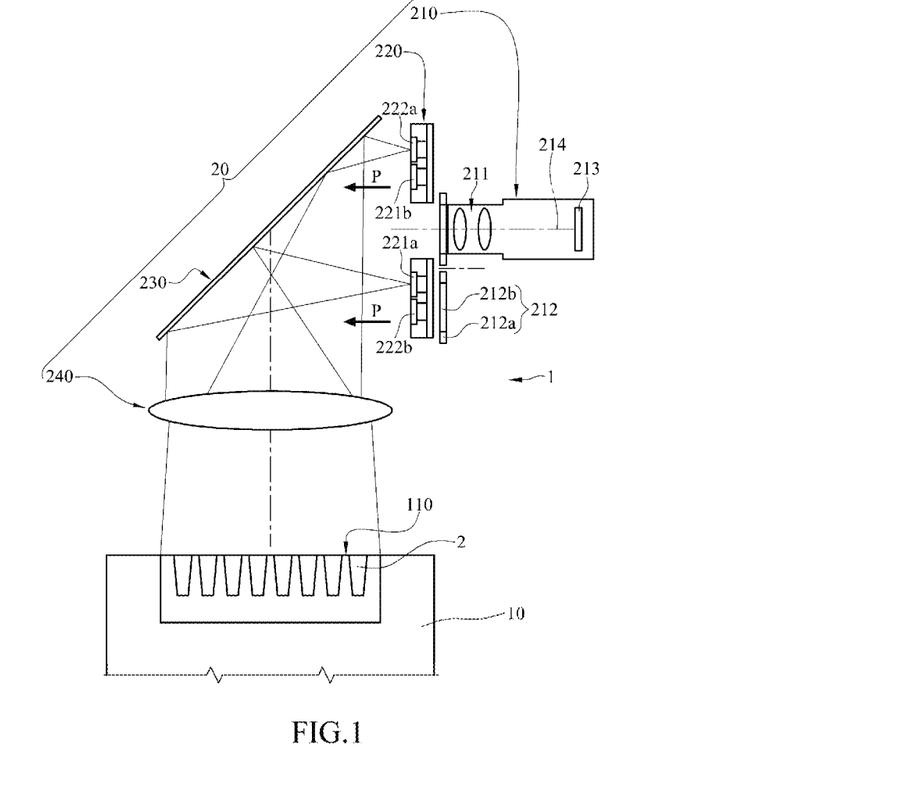
FIG. 1 is a schematic view of a first embodiment of the automatic fluorescence detection system and DNA specimens in accordance with the present invention.
Figure 2:
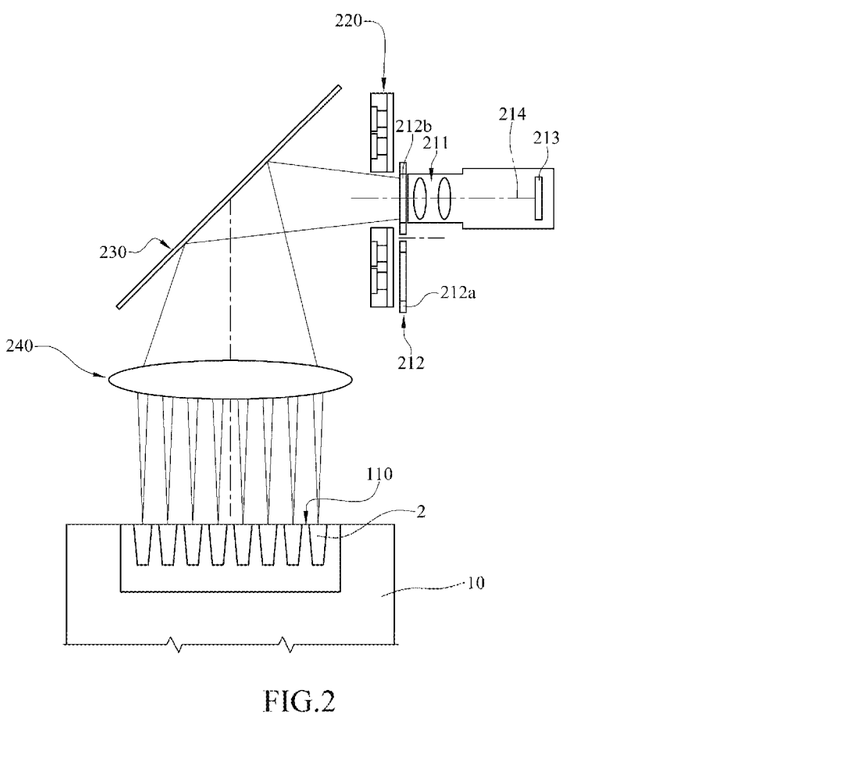
FIG. 2 shows another state of FIG. 1, where fluorescence of the DNA specimens are excited.

Refer now to both FIG. 1 and FIG. 2; where FIG. 1 is a schematic view of a first embodiment of the automatic fluorescence detection system and DNA specimens in accordance with the present invention, and FIG. 2 shows another state of FIG. 1 with fluorescence of the DNA specimens being excited. In this embodiment, the automatic fluorescence detection system 1 includes a base 10 and an optical assembly 20.

The base 10 provides thereon a detecting region 110, and the detection region 110 can have, but not limited to, a size pairing a centrifuge tube rack.

Figure 3:
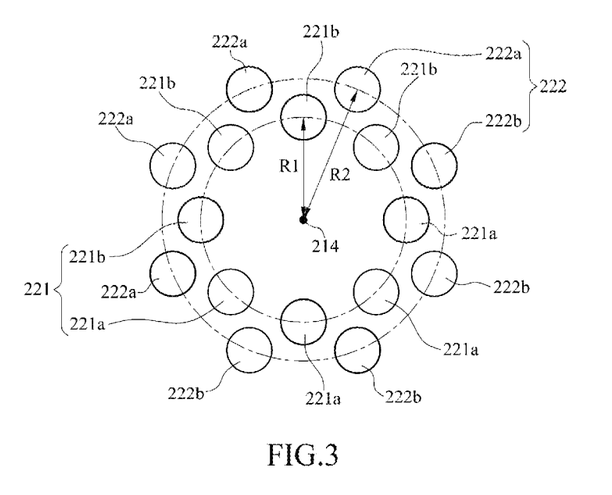
FIG. 3 is a schematic view of the illumination device of FIG. 1.
Figure 4A:
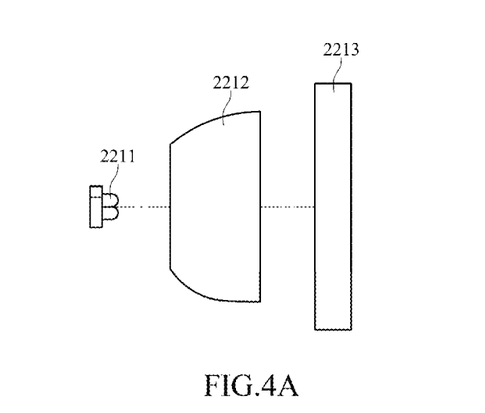
FIG. 4A is a schematic exploded view of the illumination unit in the first annular illumination module of FIG. 3.
Figure 4B:
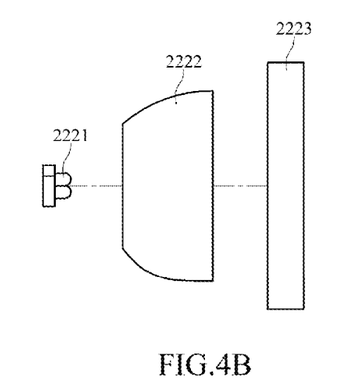
FIG. 4B is a schematic exploded view of the illumination unit in the second annular illumination module of FIG. 3.

Further, refer to FIG. 3 through FIG. 4B; where FIG. 3 is a schematic view of the illumination device of FIG. 1, FIG. 4A is a schematic exploded view of the illumination unit in the first annular illumination module of FIG. 3, and FIG. 4B is a schematic exploded view of the illumination unit in the second annular illumination module of FIG. 3. The optical assembly 20 includes a fluorescent image-capturing device 210, an illumination device 220, a reflector 230 and a field lens 240.

The fluorescent image-capturing device 210 includes an optical lens 211, a filter module 212 and an electronic photon-sensing component 213. The optical lens 211 defines two opposite sides; an object side between the optical lens 211 and the base 10 (the right-hand side in the figure), and an image side opposing the object side with respect to the optical lens 211 (the left-hand side in the figure). The filter module 212 is disposed at the object side of the optical lens 211, while the electronic photon-sensing component 213 is disposed at the image side of the optical lens 211. The filter module 212 includes a rotational base 212a and at least one filter component 212b furnished on the rotational base 212a. The filter component 212b can be, but not limited to, a color-filtering plate that can be used for filtering visible lights. In addition, the electronic photon-sensing component 213 can be, but not limited to, a CCD.

The illumination device 220 includes a first annular illumination module 221 and a second annular illumination module 222, both surrounding a center axis 214 of the fluorescent image-capturing device 210. The first annular illumination module 221 includes a plurality of illumination units 221a and 221b in a staggered arrangement. Each of the illumination units 221a, 221b includes an LED cluster 2211 including a plurality of LEDs, a light-collecting component 2212 and a color-filtering plate 2213. The LED of the LED cluster 2211 can be, but not limited to, an ultraviolet LED. The light-collecting component 2212 can be, but not limited to, a metallic reflective cup surrounding the LED cluster 2211. The light-collecting component 2212 is disposed between the color-filtering plate 2213 and the LED cluster 2211. In this embodiment, the illumination units 221a and the illumination units 221b of the first annular illumination module 221 can emit excitation lights with different wavelengths. In detail, the LED of the LED cluster 2211 of the illumination unit 221a can emit an ultraviolet with a wavelength ranging from 400 nm to 420 nm, for example. On the other hand, the LED of the LED cluster 2211 of the illumination unit 221b can emit an ultraviolet with a shorter wavelength ranging from 370 nm to 390 nm, for example. Also, it shall be noted that the number of the LEDs within the LED cluster 2211 are not particularly limited in accordance with the present invention.

The second annular illumination module 222 includes a plurality of illumination units 222a and 222b in a staggered arrangement. Each of the illumination units 222a, 222b includes an LED cluster 2221 including a plurality of LEDs, a light-collecting component 2222 and a color-filtering plate 2223. The light-collecting component 2222 surrounds the LED cluster 2221. The light-collecting component 2222 is disposed between the color-filtering plate 2223 and the LED cluster 2221. In this embodiment, the illumination units 222a and the illumination units 222b of the second annular illumination module 222 can emit excitation lights with different wavelengths. In detail, the LED of the LED cluster 2221 of the illumination unit 222a can emit an ultraviolet same as that emitted by the LED of the LED cluster 2211 of the illumination unit 221a with a wavelength ranging from 400 nm to 420 nm, for example. On the other hand, the LED of the LED cluster 2221 of the illumination unit 222b can emit an ultraviolet same as that emitted by the LED of the LED cluster 2211 of the illumination unit 221b. Also, it shall be noted that the number of the LEDs within the LED cluster 2221 are not particularly limited in accordance with the present invention.

The first annular illumination module 221 and the second annular illumination module 222 have different outer diameters. As shown in FIG. 3, a distance R1 from any of the illumination units 221a, 221b of the first annular illumination module 221 to the center axis 214 (i.e., the optical axis) of the fluorescent image-capturing device 210 is smaller than another distance R2 from any of the illumination units 222a, 222b of the second annular illumination module 221 to the center axis 214 of the fluorescent image-capturing device 210. In addition, either the illumination units 221a, 221b of the first annular illumination module 221 or the illumination units 222a, 222b of the second annular illumination module 222 are in a staggered arrangement. However, the staggered arrangement for the illumination units 221a, 221b, 222a, 222b and the wavelengths of the excitation lights are not used to limit the present invention.

The reflector 230 can be, but not limited to, a plane mirror, and is disposed at an illumination side of the illumination device 220. The reflector 230 can reflect the lights from the first annular illumination module 221 and the second annular illumination module 222. The field lens 240 can be, but not limited to, a bi-convex lens, and is disposed between the detecting region 110 of the base 10 and the reflector 230. In addition, an area of the effective optical region of the field lens 240 is larger than or equal to another area of the detecting region 110. Functions of the reflector 230 and the field lens 240 would be elucidated lately.

In the following description, a quantitative real-time polymerase chain reaction is performed by the automatic fluorescence detection system 1. As shown in FIG. 1, the detecting region 110 of the base 10 is loaded with a plurality of centrifuge tubes for containing the specimens 2. In this embodiment, the specimen 2 is a DNA fragment that has experienced already at least one polymerase chain reaction and been combined with the fluorescent dyes.

The controller (not shown in the figure) of the automatic fluorescence detection system 1 instructs the illumination units 221a of the first annular illumination module 221 and the illumination units 222a of the second annular illumination module 222 emit simultaneously the ultraviolets to excite the fluorescent dyes. The ultraviolets travel along a light-traveling path P to radiate the detecting region 110. In this embodiment, the light-traveling path P is substantially parallel to the center axis 214 of the fluorescent image-capturing device 210. When the ultraviolets travel along the light-traveling path P to reach the reflector 230, the ultraviolets would be reflected by the reflector 230 so as to alter the transmission direction, and then further to reach the field lens 240. While the ultraviolets pass the field lens 240, the field lens 240 would refract the ultraviolets, such that the optical field of the ultraviolets would be changed. The ultraviolets passing the field lens 240 would be finally projected onto the detecting region 110 so as to excite the fluorescent dyes bound on the DNA fragments, and then fluorescence of the corresponding specimens 2 would be induced. In this embodiment, the field lens 240 is featured to adjust the optical field of the ultraviolets, to distribute evenly the energy of the ultraviolets, and further to achieve beam shaping.

As shown in FIG. 2, the specimen 2 would be excited by the ultraviolets with a beam-shaped optical field to generate the fluorescence. The fluorescence would pass the field lens 240 and the reflector 230, and finally project onto the fluorescent image-capturing device 210 along the optical axis 214 (i.e., the center axis). After the fluorescence enters the fluorescent image-capturing device 210, it orderly passes the filter module 212 and the optical lens 211, and is finally received by the electronic photon-sensing component 213, such that the electronic photon-sensing component 213 can produce fluorescent images corresponding to the specimens 2.

In this embodiment, the reflector 230 can alter the transmission direction of the ultraviolets emitted by the first annular illumination module 221 and the second annular illumination module 222. However, in some other embodiments, specific passive optical components such as the optical splitter and the prism may be used to alter the transmission direction.

Figure 5:
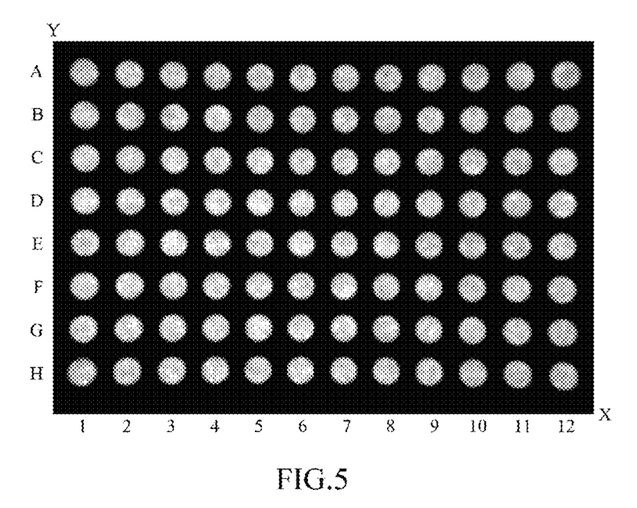
FIG. 5 is a schematic view of fluorescent images of the DNA specimens captured at FIG. 2.
Figure 6:
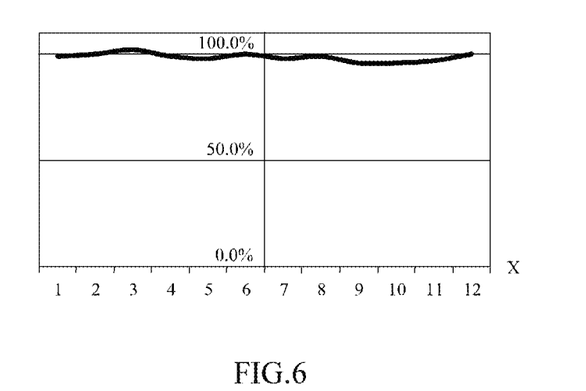
FIG. 6 shows schematically variations of fluorescence intensities in an X-axial direction for the fluorescent images of FIG. 5.
Figure 7:
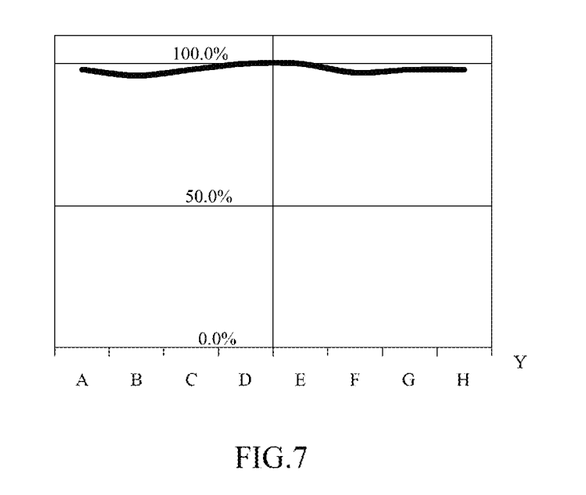
FIG. 7 shows schematically variations of fluorescence intensities in a Y-axial direction for the fluorescent images of FIG. 5.

Refer now to FIG. 5 to FIG. 7; where FIG. 5 is a schematic view of fluorescent images of the DNA specimens captured at FIG. 2, FIG. 6 shows schematically variations of fluorescence intensities in an X-axial direction for the fluorescent images of FIG. 5, and FIG. 7 shows schematically variations of fluorescence intensities in a Y-axial direction for the fluorescent images of FIG. 5. In the fluorescent image of FIG. 5, each white spot is correspond to each centrifuge tube that is loaded on the base 10.

As shown in FIG. 6, the fluorescent images along a direction from scale 1 to scale 12 demonstrate uniformity in the distribution of the fluorescence intensities. Further, the minimal fluorescence intensity of the fluorescent images at the peripheral area thereof (such as the fluorescent images at scales 9, 10) is about 90% fluorescence intensity of the fluorescent images at the central portion thereof (such as the fluorescent images at scales 6, 7). As shown in FIG. 7, the fluorescent images along a direction from scale A to scale H demonstrate uniformity in the distribution of the fluorescence intensities. Further, the minimal fluorescence intensity of the fluorescent images at the peripheral area thereof (such as the fluorescent images at scales B, F) is about 90% fluorescence intensity of the fluorescent images at the central portion thereof (such as the fluorescent images at scales D, E).

Figure 8:
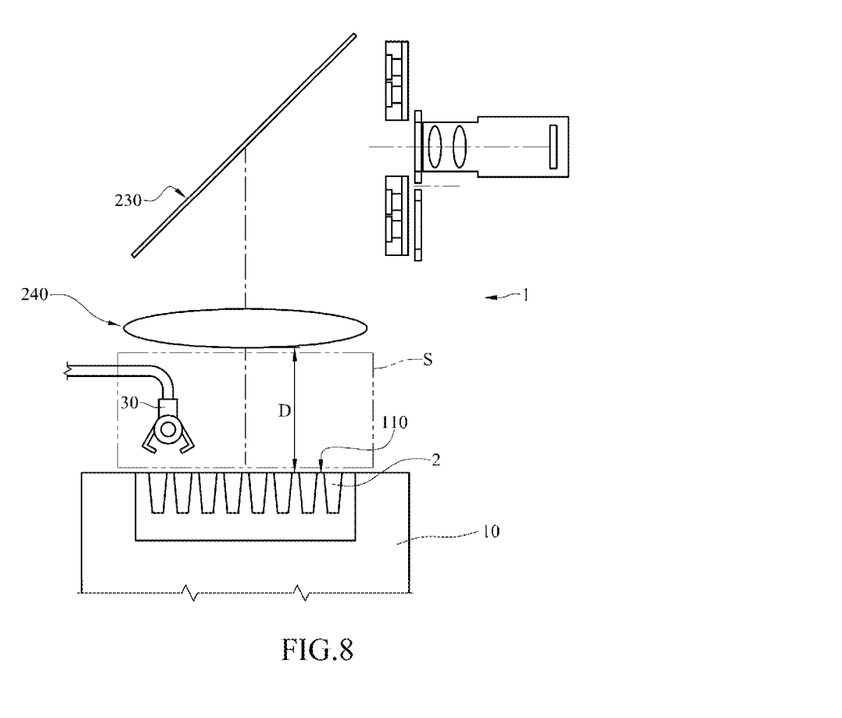
FIG. 8 is a schematic view of a specimen-picking device and the automatic fluorescence detection system of FIG. 1 in accordance with the present invention.

In the art, while the conventional fluorescence detection system performs the quantitative real-time polymerase chain reaction, the specimens 2 are loaded and unloaded to the base 10 manually, from which the conventional fluorescence detection system cannot be relevant for majority testing. To overcome the aforesaid shortcoming, the automatic fluorescence detection system 1 provided by the present invention is specifically arranged to meet an automation demand for performing the quantitative real-time polymerase chain reactions. In this demand, the automatic quantitative real-time polymerase chain reaction can upload/download the specimens 2 automatically with respect to the base 10. Referring now to FIG. 8, a schematic view of a specimen-picking device and the automatic fluorescence detection system of FIG. 1 in accordance with the present invention is shown. In this embodiment, the automatic fluorescence detection system 1 further includes a specimen-picking device 30, which is a non-optical device movably disposed at the base 10 or the automatic fluorescence detection system 1. The specimen-picking device 30 can be, but not limited to, a clamp mechanism having a vertical rack. The field lens 240 of the optical assembly 20 and the detecting region 110 of the base 10 are spaced to provide a work space S for accommodating the specimen-picking device 30. When the specimens 2 shall be unloaded from or loaded on the base 10, the specimen-picking device 30 can displace with respect to the base 10 into the work space S to pick up or drop the specimens 2. In this embodiment, the spacing D between the field lens 240 and the detecting region 110 is ranged from 15.0 cm to 30.0 cm, so that a sufficient work space S can be provided to accommodate the specimen-picking device 30 and to allow the specimen-picking device 30 to work normally. In this embodiment, the spacing between the field lens 240 and the detecting region 110 is the air gap between the field lens 240 and the detecting region 110.

In addition, in this embodiment, the illumination units 221a, 221b of the first annular illumination module 221 can emit lights with different wavelengths, and the illumination units 222a, 222b of the second annular illumination module 222 can also emit lights with different wavelengths. Further, the controller of the automatic fluorescence detection system 1 can instruct the illumination units 221a, 222a to emit simultaneously lights with longer wavelengths, or instruct the illumination units 221b, 222b to emit simultaneously lights with shorter wavelengths. Thereby, the automatic fluorescence detection system 1 can be better applied to detect DNA fragments having different fluorescent dyes automatically.

Figure 9:
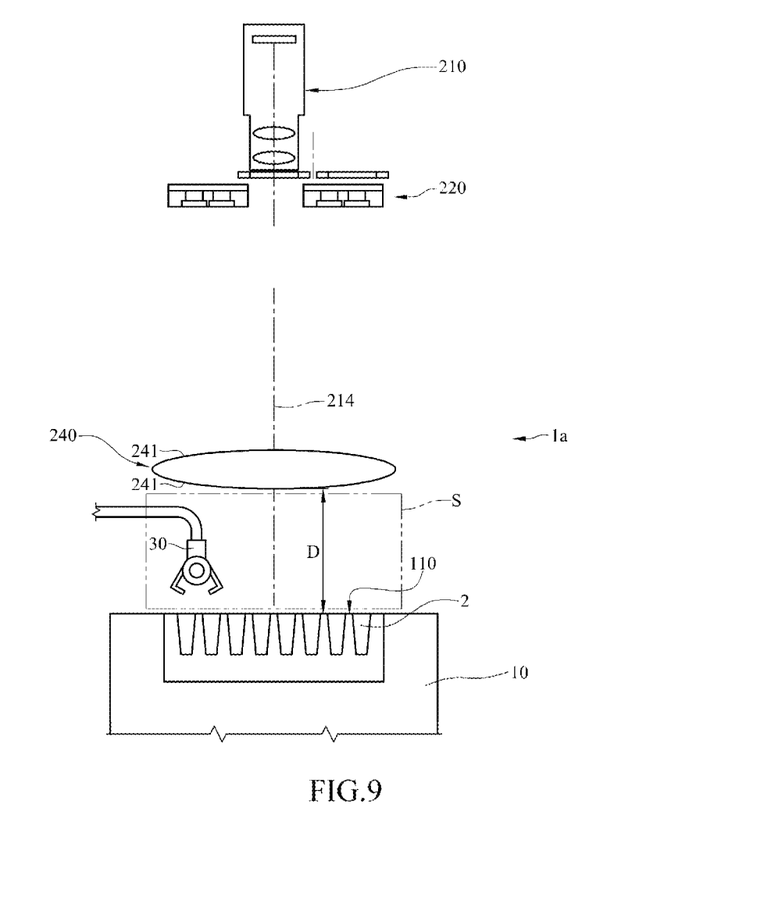
FIG. 9 is a schematic view of the specimen-picking device of FIG. 8 and a second embodiment of the automatic fluorescence detection system in accordance with the present invention.

In the first embodiment, the center axis of the fluorescent image-capturing device is perpendicular to the optical axis of the field lens, such that the reflector can be used to alter the traveling directions of the excited ultraviolets and the induced fluorescence. However, it shall be understood as well that the present invention does not limit the arrangement of elements into a specific embodiment. As shown in FIG. 9, a schematic view of the specimen-picking device of FIG. 8 and a second embodiment of the automatic fluorescence detection system in accordance with the present invention is shown. Since the second embodiment is largely resembled to the first embodiment, thus details for the common elements would be omitted herein.

In this embodiment, the automatic fluorescence detection system 1a includes the base 10 and the fluorescent image-capturing device 210, both aligning the same optical axis of the field lens 240. In detail, the field lens 240 has two opposite lens surfaces 241. The detecting region 110 of the base 10 faces one of the lens surfaces 241, while the fluorescent image-capturing device 210 and the illumination device 220 face another lens surface 241. The center axis 214 of the fluorescent image-capturing device 210 is substantially overlapped with the optical axis of the field lens 240.

Figure 10:
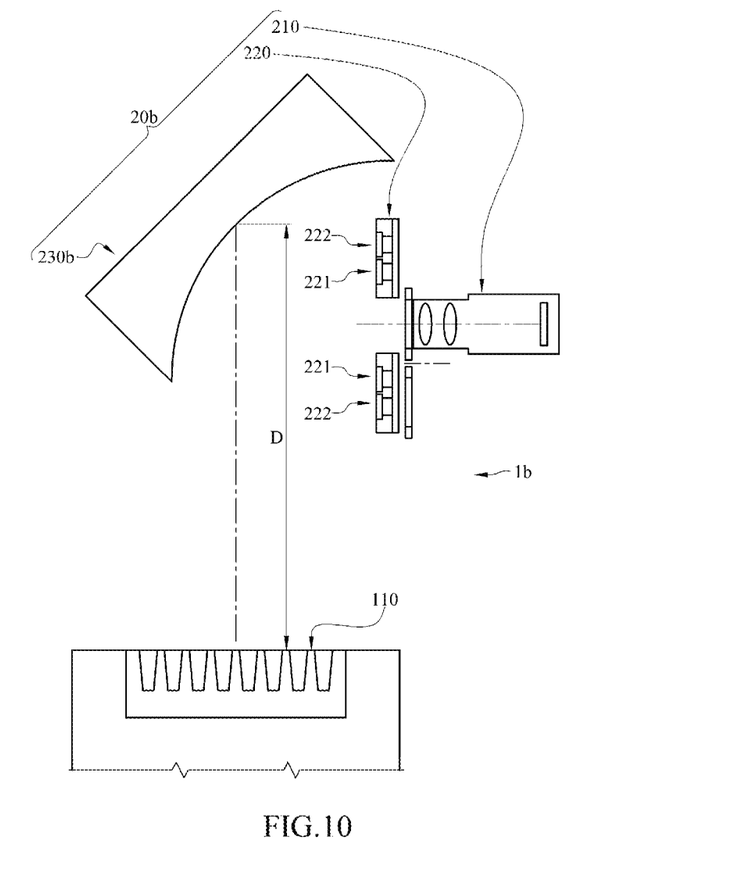
FIG. 10 is a schematic view of a third embodiment of the automatic fluorescence detection system in accordance with the present invention.

FIG. 10 is a schematic view of a third embodiment of the automatic fluorescence detection system in accordance with the present invention. Since the third embodiment is largely resembled to the first embodiment, thus details for the common elements would be omitted herein.

In this embodiment, the automatic fluorescence detection system 1b further includes an optical assembly 20b. The optical assembly 20b includes the fluorescent image-capturing device 210, the illumination device 220 and a concave reflector 230b. The fluorescent image-capturing device 210 and the illumination device 220 of the third embodiment are resembled to those in the first embodiment, and thus details thereabout would be omitted herein.

The concave reflector 230b is disposed to the illumination side of the illumination device 220. The lights emitted by the first annular illumination module 221 and the second annular illumination module 222 would be reflected by the concave reflector 230b, and then are projected onto the detecting region 110. The concave reflector 230b adopted in this embodiment can alter the optical transmission direction and the optical field, and thus no additional field lens is needed between the concave reflector 230b and the detecting region 110. Therefore, more space between the concave reflector 230b and the detecting region 110 can be available for arranging a specimen-picking device. Similar to the first embodiment, the spacing D (air gap) between the concave reflector 230b and the detecting region 110 can be, but not limited to be, ranged from 15.0 cm to 30.0 cm.

In summary, the automatic fluorescence detection system provided by the present invention adopts the illumination device having the annular illumination module to pair the field lens or the concave reflector, so that the optical field can be adjusted to make the excitation lights uniformly distributed. Thereupon, fluorescences with uniform intensities can be excited by the excitation lights upon DNA fragments at both the central portion and peripheral areas of the detecting region. Thus, the fluorescence intensity of the fluorescent image captured by the fluorescent image-capturing device at the peripheral area of the detecting region is about 90% the fluorescence intensity of the fluorescent image captured by the fluorescent image-capturing device at the central portion thereof, such that the testing of DNA density can be much accurate.

In addition, a sufficient work space between the field lens and the detecting region or between the concave reflector and the detecting region can be provided to accommodate the specimen-picking device. Thus, the automatic fluorescence detection system of this present invention applies the specimen-picking device to upload or download the centrifuge tubes containing DNA fragments, such that the automation in performing the quantitative real-time polymerase chain reaction cam be fulfilled.

While the present invention has been particularly shown and described with reference to a preferred embodiment, it will be understood by those skilled in the art that various changes in form and detail may be without departing from the spirit and scope of the present invention.

What is claimed is:

1. An automatic fluorescence detection system, comprising:
   a base, having a detecting region; and
   an optical assembly, including:
      a fluorescent image-capturing device;
      an illumination device, structured into a two-concentric-ring pattern, including a first annular illumination module and a second annular illumination module surrounding a center axis of the fluorescent image-capturing device, the first annular illumination module including a plurality of illumination units distributed along a circle in a staggered arrangement, the second annular illumination module including a plurality of another illumination units distributed along another circle in another staggered arrangement, light emitted by the first annular illumination module and the second annular illumination module traveling along a light-traveling path to project onto the detecting region, a radius of the circle for the first annular illumination module to the center axis being smaller than another radius of the another circle for the second annular illumination module to the center axis, wherein the light-travelling path of the light leaving the first annular illumination module and the second annular illumination module is parallel to the center axis of the fluorescent image-capturing device; and
      a field lens, disposed in correspondence with the detecting region, spacing between the field lens and the detecting region being ranged from 15.0 cm to 30.0 cm.

2. The automatic fluorescence detection system of claim 1, wherein the optical assembly further includes a reflector, the field lens is disposed between the base and the reflector, and the light emitted by the first annular illumination module and the second annular illumination module is reflected by the reflector to further project onto the detecting region.

3. The automatic fluorescence detection system of claim 1, wherein the plurality of illumination units of the first annular illumination module emit light with different wavelengths, and the plurality of another illumination units of the second annular illumination module emit another light with different wavelengths.

4. The automatic fluorescence detection system of claim 3, wherein the light of a portion of the plurality of illumination units of the first annular illumination module and the light of a portion of the plurality of another illumination units of the second annular illumination module have the same wavelength.

5. The automatic fluorescence detection system of claim 1, wherein each of the plurality of illumination units and another illumination units includes at least one LED, a light-collecting component surrounding the at least one LED, and a color-filtering plate, and the light-collecting component is disposed between the at least one LED and the color-filtering plate.

6. The automatic fluorescence detection system of claim 1, wherein the base and the fluorescent image-capturing device are disposed along an optical axis of the field lens.

7. An automatic fluorescence detection system, comprising:
   a base, having a detecting region; and
   an optical assembly, including:
      a fluorescent image-capturing device;
      an illumination device, structured into a two-concentric-ring pattern, including a first annular illumination module and a second annular illumination module surrounding a center axis of the fluorescent image-capturing device, the first annular illumination module including a plurality of illumination units distributed along a circle in a staggered arrangement, the second annular illumination module including a plurality of another illumination units distributed along another circle in another staggered arrangement, a radius of the circle for the first annular illumination module to the center axis being smaller than another radius of the another circle for the second annular illumination module to the center axis, light emitted by the first annular illumination module and the second annular illumination module traveling along a light-traveling path being parallel to the center axis of the fluorescent image-capturing device; and
      a concave reflector, disposed in correspondence with the detecting region, the light emitted by the first annular illumination module and the second annular illumination module being reflected by the concave reflector and then projecting onto the detecting region, minimal spacing between the concave reflector and the detecting region being ranged from 15.0 cm to 30.0 cm.

8. An automatic fluorescence detection system, comprising:
   a base, having a detecting region;
   an optical assembly, including a fluorescent image-capturing device, an illumination device and a field lens, light emitted by the illumination device traveling along a light-traveling path to project onto the detecting region, the field lens being disposed in correspondence with the detecting region, having a work space between the field lens and the detecting region, wherein the illumination device structured into a two-concentric-ring pattern having a first annular illumination module and a second annular illumination module surrounding a center axis of the fluorescent image-capturing device, the first annular illumination module includes a plurality of illumination units distributed along an inner circle in a staggered arrangement, and the second annular illumination module including a plurality of another illumination units distributed along an outer circle in another staggered arrangement; and
   a specimen-picking device, being movably in the work space with respect to the base.

* * * * *